(12) United States Patent
Tamarkin et al.

(10) Patent No.: US 7,575,739 B2
(45) Date of Patent: Aug. 18, 2009

(54) FOAMABLE IODINE COMPOSITION

(75) Inventors: Dov Tamarkin, Maccabim (IL); Doron Friedman, Karmei Yosef (IL); Meir Eini, Ness Ziona (IL)

(73) Assignee: Foamix Ltd., Ness Ziona (IL)

( * ) Notice: Subject to any disclaimer, the term of this patent is extended or adjusted under 35 U.S.C. 154(b) by 897 days.

(21) Appl. No.: 10/835,359

(22) Filed: Apr. 28, 2004

(65) Prior Publication Data

US 2004/0265240 A1 Dec. 30, 2004

Related U.S. Application Data

(60) Provisional application No. 60/466,094, filed on Apr. 28, 2003.

(51) Int. Cl.
*A01N 25/02* (2006.01)
(52) U.S. Cl. ....................................................... 424/43
(58) Field of Classification Search .................... 424/43
See application file for complete search history.

(56) References Cited

U.S. PATENT DOCUMENTS

| | | | |
|---|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,968,628 A | 1/1961 | Reed |
| 3,062,715 A | 11/1962 | Reese |
| 3,141,821 A | 7/1964 | Compeau |
| 3,144,386 A | 8/1964 | Brighttenback |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,869 A | 8/1966 | Corsette |
| 3,303,970 A | 2/1967 | Breslau et al. |
| 3,330,730 A | 7/1967 | Hernaadez |
| 3,369,034 A | 2/1968 | Chalmers |
| 3,395,215 A | 7/1968 | Warren |
| 3,419,658 A | 12/1968 | Amsdon |
| 3,559,890 A | 2/1971 | Brooks et al. |
| 3,561,262 A | 2/1971 | Borocki |
| 3,577,518 A | 5/1971 | Shepherd |
| 3,770,648 A | 11/1973 | Mackles |
| 3,787,566 A | 1/1974 | Gauvreau |
| 3,882,228 A | 5/1975 | Boncey et al. |
| 3,886,084 A | 5/1975 | Vassiliades |
| 3,912,665 A | 10/1975 | Spitzer et al. |
| 3,923,970 A | 12/1975 | Breuer |
| 3,929,985 A | 12/1975 | Webb, Jr. |
| 3,966,090 A * | 6/1976 | Prussin et al. ................. 222/94 |
| 3,970,584 A | 7/1976 | Hart et al. |
| 3,993,224 A | 11/1976 | Harrison |
| 4,110,426 A | 8/1978 | Barnhurst |
| 4,124,149 A | 11/1978 | Spitzer et al. |
| 4,145,411 A | 3/1979 | Mende |
| 4,160,827 A | 7/1979 | Cho et al. |
| 4,213,979 A | 7/1980 | Levine |
| 4,214,000 A | 7/1980 | Papa |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,326 A | 9/1981 | Nazzaro-Porro et al. |
| 4,299,826 A | 11/1981 | Luedder |
| 4,385,161 A | 5/1983 | Caunt et al. |
| 4,386,104 A | 5/1983 | Nazzaro-Porro |
| 4,522,948 A | 6/1985 | Walker |
| 4,529,601 A | 7/1985 | Broberg et al. |
| 4,529,605 A | 7/1985 | Lynch et al. |
| 4,576,961 A | 3/1986 | Lorck et al. |
| 4,627,973 A | 12/1986 | Moran |
| 4,628,063 A | 12/1986 | Haines et al. |
| 4,673,569 A | 6/1987 | Shernov et al. |
| 4,752,465 A | 6/1988 | Mackles |

(Continued)

FOREIGN PATENT DOCUMENTS

DE 10138495 2/2003

(Continued)

OTHER PUBLICATIONS

Martindale, The extra pharmacopoeia [28th] edition, Eds.: Reynolds, J.E.F. and Prasad, A.B., The Pharmaceutical Press, London, 1982, pp. 862-864.

(Continued)

*Primary Examiner*—Johann R Richter
*Assistant Examiner*—Kristie L Brooks
(74) *Attorney, Agent, or Firm*—Wilmer Cutler Pickering Hale and Dorr LLP

(57) ABSTRACT

The present invention is related to a foamable composition of matter comprising iodine, water, a foam adjuvant, a surface-active agent and a gelling agent. This foamable composition, which may be provided in a propellant free foaming device, or alternatively may further comprise a propellant, evolves into foam, which is effective in the topical treatment and prevention of various skin disorders.

25 Claims, 1 Drawing Sheet

U.S. PATENT DOCUMENTS

| | | |
|---|---|---|
| 4,784,842 A | 11/1988 | London et al. |
| 4,804,674 A | 2/1989 | Curtis-Prior |
| 4,808,388 A | 2/1989 | Beutler et al. |
| 4,822,614 A | 4/1989 | Rodero |
| 4,827,378 A | 5/1989 | Gillan et al. |
| 4,836,217 A | 6/1989 | Fischer |
| 4,837,378 A | 6/1989 | Borgman |
| 4,863,900 A | 9/1989 | Pollock et al. |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,913,893 A | 4/1990 | Varco et al. |
| 4,957,732 A | 9/1990 | Grollier et al. |
| 4,963,351 A | 10/1990 | Weston |
| 4,981,677 A | 1/1991 | Thau |
| 4,981,845 A | 1/1991 | Pereira |
| 4,992,478 A | 2/1991 | Geria |
| 5,002,680 A | 3/1991 | Schmidt et al. |
| 5,007,556 A | 4/1991 | Lover |
| 5,015,471 A | 5/1991 | Birtwistle et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,089,252 A | 2/1992 | Grollier et al. |
| 5,094,853 A | 3/1992 | Hagarty |
| 5,100,917 A | 3/1992 | Flynn et al. |
| 5,130,121 A | 7/1992 | Kopolow et al. |
| 5,135,915 A | 8/1992 | Czarniecki et al. |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,230,897 A | 7/1993 | Griffin et al. |
| 5,254,334 A | 10/1993 | Ramirez et al. |
| 5,262,407 A | 11/1993 | Leveque et al. |
| 5,279,819 A | 1/1994 | Hayes |
| 5,300,286 A | 4/1994 | Gee |
| 5,301,841 A | 4/1994 | Fuchs et al. |
| 5,308,643 A | 5/1994 | Osipow et al. |
| 5,314,904 A | 5/1994 | Egidio et al. |
| 5,326,557 A | 7/1994 | Glover et al. |
| 5,352,437 A | 10/1994 | Nakagawa et al. |
| 5,380,761 A | 1/1995 | Szabo |
| 5,384,308 A | 1/1995 | Henkin |
| 5,385,943 A | 1/1995 | Nazzaaro-Porro |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,578,315 A | 11/1996 | Chien et al. |
| 5,589,157 A | 12/1996 | Hatfield |
| 5,589,515 A | 12/1996 | Suzuki et al. |
| 5,603,940 A | 2/1997 | Candau et al. |
| 5,605,679 A | 2/1997 | Hansenne et al. |
| 5,614,171 A | 3/1997 | Clavenna et al. |
| 5,635,469 A | 6/1997 | Fowler et al. |
| 5,641,480 A | 6/1997 | Vermeer |
| 5,650,554 A | 7/1997 | Moloney |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,700,396 A | 12/1997 | Suzuki et al. |
| 5,716,611 A * | 2/1998 | Oshlack et al. ........... 424/78.25 |
| 5,719,122 A | 2/1998 | Chiodini et al. |
| 5,719,197 A | 2/1998 | Kanios et al. |
| 5,730,964 A | 3/1998 | Waldstreicher |
| 5,733,558 A | 3/1998 | Breton et al. |
| 5,753,245 A | 5/1998 | Fowler et al. |
| 5,759,520 A | 6/1998 | Sachetto |
| 5,759,579 A | 6/1998 | Singh et al. |
| 5,783,202 A | 7/1998 | Tomlinson et al. |
| 5,792,922 A | 8/1998 | Moloney et al. |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,840,744 A | 11/1998 | Borgman |
| 5,846,983 A | 12/1998 | Sandborn |
| 5,856,452 A | 1/1999 | Moloney et al. |
| 5,866,040 A | 2/1999 | Nakama et al. |
| 5,877,216 A | 3/1999 | Place et al. |
| 5,879,469 A | 3/1999 | Avram et al. |
| 5,885,581 A | 3/1999 | Massand |
| 5,889,028 A | 3/1999 | Sandborn et al. |
| 5,891,458 A | 4/1999 | Britton |
| 5,902,574 A | 5/1999 | Stoner et al. |
| 5,902,789 A | 5/1999 | Stoltz |
| 5,911,981 A | 6/1999 | Dahms et al. |
| 5,922,331 A | 7/1999 | Mausner |
| 5,948,682 A | 9/1999 | Moloney |
| 5,951,993 A | 9/1999 | Scholz et al. |
| 5,952,392 A | 9/1999 | Katz et al. |
| 5,961,957 A | 10/1999 | McAnalley |
| 5,972,310 A | 10/1999 | Sachetto |
| 5,993,846 A | 11/1999 | Friedman et al. |
| 6,019,967 A | 2/2000 | Breton et al. |
| 6,033,647 A | 3/2000 | Touzan et al. |
| 6,042,848 A | 3/2000 | Lawyer et al. |
| 6,071,536 A | 6/2000 | Suzuki et al. |
| 6,087,317 A | 7/2000 | Gee |
| 6,090,772 A | 7/2000 | Kaiser et al. |
| 6,093,408 A | 7/2000 | Hasenoehrl et al. |
| 6,113,888 A | 9/2000 | Castro et al. |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,210,742 B1 | 4/2001 | Deckers et al. |
| 6,221,381 B1 | 4/2001 | Shelford et al. |
| 6,224,888 B1 | 5/2001 | Vatter |
| 6,251,369 B1 | 6/2001 | Stoltz |
| 6,258,374 B1 | 7/2001 | Friess et al. |
| 6,287,546 B1 | 9/2001 | Reich et al. |
| 6,294,550 B1 | 9/2001 | Place |
| 6,306,841 B1 | 10/2001 | Place |
| 6,333,362 B1 | 12/2001 | Lorant |

| | | |
|---|---|---|
| 6,358,541 B1 | 3/2002 | Goodman |
| 6,372,234 B1 | 4/2002 | Deckers et al. |
| 6,383,471 B1 | 5/2002 | Chen et al. |
| 6,395,300 B1 | 5/2002 | Straub et al. |
| 6,410,036 B1 | 6/2002 | De Rosa et al. |
| 6,423,323 B2 | 7/2002 | Neubourg |
| 6,433,033 B1 | 8/2002 | Isobe et al. |
| 6,437,006 B1 | 8/2002 | Yoon et al. |
| 6,468,989 B1 | 10/2002 | Chang |
| 6,514,487 B1 | 2/2003 | Barr |
| 6,524,594 B1 | 2/2003 | Santora et al. |
| 6,536,629 B2 | 3/2003 | van der Heijden |
| 6,544,530 B1 | 4/2003 | Friedman |
| 6,582,710 B2 | 6/2003 | Deckers et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,672,483 B1 | 1/2004 | Roy et al. |
| 6,730,288 B1 | 5/2004 | Abram |
| 6,753,167 B2 | 6/2004 | Moloney et al. |
| 6,765,001 B2 | 7/2004 | Gans et al. |
| 6,777,591 B1 | 8/2004 | Chaudhary |
| 6,946,120 B2 | 9/2005 | Wai-Chiu So et al. |
| 7,029,659 B2 | 4/2006 | Abram et al. |
| 7,137,536 B2 | 11/2006 | Walters et al. |
| 2001/0006654 A1 | 7/2001 | Cannell et al. |
| 2002/0032171 A1 | 3/2002 | Chen et al. |
| 2002/0035046 A1 | 3/2002 | Lukenbach et al. |
| 2002/0045659 A1 | 4/2002 | Michelet et al. |
| 2002/0048798 A1 | 4/2002 | Avery et al. |
| 2002/0072544 A1 | 6/2002 | Miller et al. |
| 2002/0098215 A1 | 7/2002 | Douin et al. |
| 2002/0134376 A1 | 9/2002 | Castro et al. |
| 2002/0143188 A1 | 10/2002 | Garvey et al. |
| 2002/0198136 A1 | 12/2002 | Mak et al. |
| 2003/0031693 A1 | 2/2003 | Breton et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0151671 A1 | 8/2004 | Abram et al. |
| 2004/0191196 A1 | 9/2004 | Tamarkin |
| 2004/0241099 A1 | 12/2004 | Popp et al. |
| 2004/0253275 A1 | 12/2004 | Eini et al. |
| 2004/0265240 A1 | 12/2004 | Tamarkin et al. |
| 2005/0031547 A1 | 2/2005 | Tamarkin et al. |
| 2005/0054991 A1 | 3/2005 | Tobyn et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0186142 A1 | 8/2005 | Tamarkin et al. |
| 2005/0186147 A1 | 8/2005 | Tamarkin et al. |
| 2005/0196414 A1 | 9/2005 | Dake et al. |
| 2005/0205086 A1 | 9/2005 | Tamarkin et al. |
| 2005/0232869 A1 | 10/2005 | Tamarkin et al. |
| 2005/0244342 A1 | 11/2005 | Friedman et al. |
| 2005/0255048 A1 | 11/2005 | Hirsh et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2006/0018937 A1 | 1/2006 | Friedman |
| 2006/0018938 A1 | 1/2006 | Neubourg |
| 2006/0057168 A1 | 3/2006 | Larm |
| 2006/0193789 A1 | 8/2006 | Tamarkin et al. |
| 2006/0233721 A1 | 10/2006 | Tamarkin et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2007/0020213 A1 | 1/2007 | Tamarkin et al. |
| 2007/0059253 A1 | 3/2007 | Popp et al. |
| 2007/0069046 A1 | 3/2007 | Eini et al. |
| 2007/0154402 A1 | 7/2007 | Trumbore et al. |
| 2007/0253911 A1 | 11/2007 | Tamarkin et al. |
| 2007/0280891 A1 | 12/2007 | Tamarkin et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0035155 A1 | 2/2008 | Dahl |
| 2008/0166303 A1 | 7/2008 | Tamarkin et al. |
| 2008/0317679 A1 | 12/2008 | Tamarkin et al. |

FOREIGN PATENT DOCUMENTS

| | | |
|---|---|---|
| EP | 0156507 A1 | 10/1985 |
| EP | 0186453 | 7/1986 |
| EP | 270 316 | 6/1988 |
| EP | 0404376 | 12/1990 |
| EP | 0488089 A1 | 6/1992 |
| EP | 0 535 327 | 4/1993 |
| EP | 0535327 | 4/1993 |
| EP | 0598412 | 11/1993 |
| EP | 0738516 | 10/1996 |
| EP | 676198 | 10/1998 |
| EP | 0979654 A1 | 2/2000 |
| EP | 1055425 A2 | 11/2000 |
| EP | 1 287 813 | 3/2003 |
| EP | 1 428 521 | 6/2004 |
| FR | 2774595 A | 8/1999 |
| GB | 808105 | 1/1959 |
| GB | 2166651 | 5/1996 |
| GB | 2337461 | 11/1999 |
| IL | 0152486 A0 | 5/2003 |
| JP | 2008040899 | 2/1996 |
| JP | 2002012513 | 1/2002 |
| WO | WO90/05774 | 5/1990 |
| WO | WO 91/11991 | 8/1991 |
| WO | WO-96/03115 | 2/1996 |
| WO | WO 96/19921 | 4/1996 |
| WO | WO 96/27376 | 9/1996 |
| WO | WO-98/18472 | 5/1998 |
| WO | WO-98/19654 | 5/1998 |
| WO | WO-98/21955 | 5/1998 |
| WO | WO-98/23291 | 6/1998 |
| WO | WO-98/36733 | 8/1998 |
| WO | WO-99/08649 | 2/1999 |
| WO | WO-99/20250 | 4/1999 |
| WO | WO-00/09082 | 2/2000 |
| WO | WO 00/15193 | 3/2000 |
| WO | WO-00/61076 | 10/2000 |
| WO | WO-00/76461 | 12/2000 |
| WO | WO-01/54679 | 8/2001 |
| WO | WO 01/70242 A2 | 9/2001 |
| WO | WO 01/70242 A3 | 9/2001 |
| WO | WO-01/82880 | 11/2001 |
| WO | WO-02/00820 | 1/2002 |
| WO | WO-02/28435 | 4/2002 |
| WO | WO-02/41847 A1 | 5/2002 |
| WO | WO-02/43490 | 6/2002 |
| WO | WO-02/062324 | 8/2002 |
| WO | WO 03/051294 | 6/2003 |
| WO | WO-03/053292 | 7/2003 |
| WO | WO-03/055445 | 7/2003 |
| WO | WO-03/075851 | 9/2003 |
| WO | WO-2004/064833 A1 | 8/2004 |
| WO | WO-2004/071479 A1 | 8/2004 |
| WO | WO 2004/112780 A1 | 12/2004 |
| WO | WO-2005/011567 A2 | 2/2005 |
| WO | WO-2005/018530 A2 | 3/2005 |
| WO | WO2005/044219 | 5/2005 |
| WO | WO-2005/076697 | 8/2005 |
| WO | WO-2005/097068 A1 | 10/2005 |
| WO | WO2005/032522 | 11/2005 |
| WO | WO-2005102539 | 11/2005 |

| | | |
|---|---|---|
| WO | WO-2006/003481 A2 | 1/2006 |
| WO | WO-2006/010589 | 2/2006 |
| WO | WO-2006/129161 | 12/2006 |
| WO | WO-2006/131784 | 12/2006 |
| WO | WO-2007/007208 | 1/2007 |
| WO | WO-2007/012977 | 2/2007 |
| WO | WO-2007/023396 | 3/2007 |
| WO | WO2007/050543 | 5/2007 |
| WO | WO-2007/054818 | 5/2007 |
| WO | WO-2007/072216 | 6/2007 |
| WO | WO-2007/085899 | 8/2007 |
| WO | WO-2007/099396 | 9/2007 |
| WO | WO-2007/039825 | 11/2007 |
| WO | WO2008/008397 | 1/2008 |
| WO | WO-2008/038147 | 4/2008 |
| WO | WO-2008/075207 | 6/2008 |

OTHER PUBLICATIONS

Wormser et al. *Letters to the* Editor, Burns, 1998, 24, 383.

Wormser et al. Arch. Toxicol., 1997, 71, 165-170.

Barry, B.W. et al, Comparative bio-availability and activity of proprietary topical corticosteroid preparations: vasoconstrictor assays on thirty-one ointments, British Journal of Dermatology, 93, 563-571, 1975.

Tamarkin, D., et al. Body Cavity Foam, U.S. Appl. No. 11/116,761, filed Apr. 28, 2005.

Tamarkin, D., et al. Moisturizing Foam Containing Lanolin, U.S. Appl. No. 11/099,942, filed Apr. 6, 2005.

Tamarkin, D., et al. Nonsteroidal Immunomodulating Kit and Composition and Uses Thereof, U.S. Appl. No. 11/078,902, filed Mar. 11, 2005.

Tamarkin, D., et al. Steroid Kit and Foamable Composition and Uses, U.S. Appl. No. 11/114,410, filed Apr. 26, 2005.

Tamarkin, D., et al. Vasoactive Kit and Composition and Uses Thereof, U.S. Appl. No. 11/124,676, filed May 9, 2005.

U.S. Appl. No. 10/911,367, Tamarkin et al., Foam Carrier Containing Amphiphilic Copolymer Gelling Agent, filed Aug. 4, 2004, Publication No. 05-0069566.

U.S. Appl. No. 10/922,555, Tamarkin et al., Foam Incorporating Eutectic Mixture, filed Aug. 20, 2004, Publication No. 05-0075407.

U.S. Appl. No. 10/835,505, Tamarkin et al., Oleaginous Pharmaceutical and Cosmetic Foam, filed Apr. 28, 2004, Publication No. 05-0031547.

U.S. Appl. No. 10/922,358, Tamarkin et al., Penetrating Pharmaceutical Foam, filed Aug. 20, 2004, Publication No. 05-0074414.

International Search Report, International Patent Application No. PCT/IB2007/003759, Foamix Ltd., Jul. 8, 2008 (2 pages).

D.W.A. Sharp Dictionary of Chemistry, Penguin Books, 1983, 3 pages.

Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.

Material Safety Data Sheet, Progesterone, Apr. 26, 2006, 5 pages.

"Licking Vaginal Dryness Without a Prescription," Estronaut, Dec. 14, 2008, 3 pages.

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Gill, A.M, et al., "Adverse Drug Reactions in a Paediatric Intensitve Care Unit," Acta Paediatr 84:438-441, 1995.

Gschnait, F., et al., "Topical Indomethacin Protects from UVB and UVA Irradiation," Arch. Dermatol. Res. 276:131-132, 1984.

Hall, Karla, "Diaper Area Hemangiomas: A Unique Set of Concerns," http://members.tripod.com/~Michelle_G/diaper.html, Dec. 1, 2008, 8 pages.

Skin Biology, CP Serum—Copper-Peptide Serum for Skin Regeneration and Reducing Wrinkles, Skin Biology, http://web.archive.org/web/20030810230608/http://www.skinbio.com/cpserum.html, Dec. 1, 2008, 21 pages.

Galligan, John et al., "Adhesive Polyurethane Liners for Anterior Restorations," J. Dent. Res., Jul.-Aug. 1968, pp. 629-632.

Innocenzi, Daniele et al., "An Open-Label Tolerability and Effiacy Study of an Aluminum Sesquichlorhydrate Topical Foam in Axilliary and Palmer Primary Hyperhidrosis," Dermatologic Therapy, vol. 21, S27-S30, 2008.

Coetzee, Nicol et al., "Acceptability and Feasibility of Micralax Applicators and of methyl Cellulose Gel Placebo for Large-Scale Clinical Trials of Vaginal Microbicides," Concise Communication, 2001, vol. 15, No. 14, pp. 1837-1842.

Pendergrass, P.B. et al., "The Shape and Dimension of the Human Vagina as Seen in Three-Dimensional Vinyl Polysiloxane Casts," Gynecol Obstet. Invest. 1996:42(3), 2 pages.

Merriam-Webster Online Dictionary, 2008, "Mousse," Merriam-Webster Online, Dec. 8, 2008 http://www.merriam-webster.com/dictionary/mousse.

Abstract for TR-436-t-Butyl Alcohol, National Toxicology Program, Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.

Denatonium Benzoate, Chemical Structure Molecular Form Reference Standard, http://www.newdruginfo.com/pharmaceopeia/usp28/v28230/usp28nf23s0_m22790.htm Accessed Dec. 9, 2008, 2 pages.

Scott, Roy R., as Published in Pharmaceutical Dosage Forms; Disperse Systems, vol. 3, Copyright 1998, 120 pages.

Flick, Cosmetic and Toiletry Formulations, vol. 5, 2nd Edition, Copyright 1996, (259-309), 63 pages.

Arisan, 8 pages, http://www.arlsankimya.com/kozmetik.htm Accessed Dec. 10, 2008.

Sigma-Aldrich, Ethanol, E7023 Ethanol 200 Proof (Absolute) for Molecular Biology, 2 pages http://www.sigmaaldrich.com/catalog/ProductDetail.do?N4=E7023SIAL&N5=SEARCH_CONCAT_PNOBRAND_KEY&F=SPEC Accessed Dec. 9, 2008.

Material Safety Data Sheet, Alcohol SDA 40B.http://www.pharmco-prod.com/pages/MSDS/SDA_40B_200.pdf  Pharmco-AAPER, Dec. 2005, 2 pages Accessed Dec. 9, 2008.

\* cited by examiner

FOAMABLE IODINE COMPOSITION

RELATED APPLICATIONS

This application claims priority under 35 U.S.C. § 119(e) to co-pending U.S. application Ser. No. 60/466,094, filed Apr. 28, 2003, and entitled "Foamable Iodine Compositions, which is incorporated in its entirety by reference.

FIELD OF THE INVENTION

The present invention relates to a foamable composition of matter comprising iodine. The invention further relates to compositions that, when provided in a suitable foaming system, evolve into foam, effective in the topical treatment of various skin conditions.

BACKGROUND OF THE INVENTION

Iodine and iodine complex preparations are widely employed as disinfectants in human and veterinary medicine. Iodine has a powerful bactericidal and fungicidal action and is also active against viruses. It is used as topical antiseptic agents for treatment of small wounds, abrasions and other skin lesions such as herpes simplex. Iodine containing compositions are used for protective treatment of a skin area to be dissected.

Iodine preparations are used in veterinary medicine as post-milking disinfecting treatment of the udders. Iodine is also effectively used for disinfection of drinking water and swimming pool water (Martindale, *The extra pharmacopoeia*, [28TH] edition, Eds.: Reynolds, J. E. F. and Prasad, A. B., *The Pharmaceutical Press*, London, 1982, pp. 862-864).

Topical iodine preparations possess counter-irritating activity in rheumatism, tenosynovitis and in inflammatory diseases of the peripheral nervous system and muscles. Additional pronounced counter-irritating activity of iodine was demonstrated against skin irritation caused by chemical and thermal stimuli. Iodine is also effective against other skin irritants such as mechlorethamine, divinylsulfone, iodoacetic acid and cantharidine (Wormser et al. *Arch. Toxicol.* (1997) 71, 165-170).

Molecular iodine ($I_2$) is practically water insoluble unless iodide (sodium or potassium salts) is present in the solution to form the water-soluble ion ($I_3^-$). Iodine can be dissolved in ethanol but precipitates in the presence of water. Thus, iodine tincture (which contains ethyl alcohol and water) must also contain iodide to form $I_3^-$ for proper dissolution.

Iodine formulations using other solvents or carriers are known. In some cases, these formulations are shown to have greater iodine solubility or improved iodine release. In some cases, the iodine formulations are demonstrated to be more potent as antiseptics than currently available commercial iodine preparations.

Post-exposure treatment with topical povidone (polyvinylpyrolidone)-iodine preparation has been shown to provide significant protection against mustard gas (sulfur mustard, SM)-induced skin lesions (Wormser et al. *Arch. Toxicol.* (1997) 71, 165-170). Studies also have shown the counter-irritating activity of povidone-iodine against thermal stimuli in humans (Wormser, *Burns* (1998) 24, 383). The experience with patients after accidental heat burns (mostly of grade I; caused by hot water or oil or by hot steam) has shown that topical application of povidone-iodine ointment immediately after the stimulus reduced the degree of skin lesions. The shorter the interval between stimulus and treatment the better the protection achieved.

U.S. Pat. No. 5,071,648 discloses a composition containing acetalized polyvinyl alcohol complexed with iodine, which releases free iodine in the presence of water.

WO 01/70242 discloses a composition including molecular iodine and tetraglycol (TG) that facilitates the dissolution of iodine, enhances its antiseptic effect, and remains stable in the presence of water, in contrast to other iodine solvents, such as ethanol, in which iodine precipitates after water addition. Povidone-iodine complex (PVP-I) may also be dissolved in TG or a TG water system. A pharmaceutically acceptable vehicle according to WO 01/70242 includes an oil/water or a water/oil emulsion, a solution, a suspension, a gel, an ointment, a patch, or an aerosol, preferably solutions, gels and washable ointments.

Despite many years of usage in topical therapy, iodine compositions are still restricted to the conventional list of dosage forms, consisting of water/oil emulsions, solutions, suspensions, gels, ointments, patch, or aerosols. All these preparations comprise liquid or semi-liquid substances, having continuous texture and consistency and possessing specific gravity of 0.7-1.1. Such preparations are disadvantageous, when intended to treat relatively large areas. They are even more disadvantageous when the area to be treated is sensitive, such as area with burns or open wounds, where rubbing a liquid or semi-solid formulation is difficult and painful.

Certain foamable formulations are known in the art.

U.S. Pat. No. 5,716,611 discloses a topical formulation comprising an anti-microbially effective amount of povidone-iodine and from 2% to about 30% of a water-soluble emollient comprising from about 1 to about 99% ethoxylated higher aliphatic alcohol and from about 1 to about 99% ethoxylated cholesterol derivative. The composition includes thickening agents and surfactants that provide foaming upon rubbing on the applied surface.

U.S. Pat. No. 6,258,374 provides a pharmaceutical composition for rectal or vaginal application containing at least two parts wherein the composition comprises (i) two or more physiologically acceptable substances each in separate parts of the composition which are such that on admixture they react to produce a physiologically acceptable gas; (ii) in at least one part of the composition a polymer stabilizer which is adapted to facilitate the formation of a water-soluble collapsible foam structure; and (iii) in at least one part of the composition a pharmaceutically active substance. One of the optional active substances is iodine.

International patent application WO 96/19921 discloses a composition having biocidal activity comprising an active agent selected from iodine or a compound or complex thereof and a polymeric solubilizing agent. The composition may be a foam.

U.S. Pat. No. 6,187,290 teaches physiologically acceptable foam including a foamable carrier separately packaged from an active ingredient. The active ingredient may be, among others, povidone-iodine. Surfactants, humectants and plasticizers may be optionally included.

U.S. Pat. No. 5,951,993 discloses a composition including a lower alcohol and water in a weight ratio of about 35:65 to 100:0, and a thickener system. The thickener system includes at least two emulsifiers, each emulsifier containing at least one hydrophobic group and at least one hydrophilic group. The composition optionally contains iodine or a complexed form of iodine. The composition is useful as a presurgical scrub replacement, a lotion or other hand preparation.

U.S. Pat. No. 5,672,634 describes a rigid, cellular PVP-I foam product, useful as an iodophor, containing about 0.1-2% cross linker and about 16-18% total inorganic iodine.

U.S. Pat. No. 5,545,401 teaches a foaming gel consisting essentially of water, povidone and iodine. In one embodiment water is added to the gel in a closed container pressurized at between 1 and 3 atmospheres with pentane so that when the mixture is returned to atmospheric pressure it spontaneously forms a foam.

U.S. Pat. No. 5,254,334 describes an anhydrous cream composition comprising (a) glycerin in an amount from about 40% to about 60% by weight based on the weight of the total composition; (b) sodium cocoyl isethionate in an amount from about 10 to about 19% by weight based on the weight of the total composition; (c) emollients in an amount from about 10 to about 40% by weight based on the weight of the total composition; and (d) sodium lauryl sulfate in an amount from about 1 to about 5% by weight based on the weight of the total composition. The composition may further comprise a foam booster or active ingredients such as PVP-iodine.

U.S. Pat. No. 4,271,149 discloses a germicidal iodine composition containing an aqueous solution of elemental iodine and at least one organic substance which slowly reacts with iodine selected from the group consisting of iodine complexing polymers, surface active agents, alcohols, polyols and water soluble solvents. The iodine composition is stable for extended storage by providing balanced sources of iodide ion in the range of about 0.025% to 0.5% and iodate ion in the range of about 0.005% to 0.2% while maintaining a pH within the range of pH 5-7. Foam stabilizers are optional components of the composition.

New topical dosage forms are desired to deliver iodine and to treat skin conditions that respond to iodine topical application. A simple-to-use breakable foam, having low specific gravity and being easily spreadable on large skin areas, is particularly desirable.

SUMMARY OF THE INVENTION

The present invention provides a foamable composition including iodine, water, a foam adjuvant, a surface-active agent and a gelling agent that is easily applied and provides high availability of iodine to the applied surface.

According to one aspect the present invention, a foamable composition includes iodine, water, a foam adjuvant, a surface active agent and a gelling agent, in the following concentrations:

- about 0.1% to about 5% by weight iodine;
- about 80% to about 99.6% by weight of at least one solvent;
- about 0.1% to about 5% by weight of at least one foam adjuvant;
- about 0.1% to about 5% by weight of at least one surface active agent; and
- about 0.1% to about 5% by weight of at least one gelling agent.

The % values presented herein are provided on a weight (w/w) basis of the total composition.

The composition according to one or more embodiments of the present invention, when provided in a suitable foaming device, forms a foam that is effective in the topical treatment of various skin conditions.

According to one or more embodiments of the present invention, the composition is provided in a plastic or glass propellant free foaming dispenser and forms a breakable or collapsible foam when dispensed from the propellant free foaming dispenser.

According to one or more embodiments of the present invention, the composition further includes a liquefied or compressed gas propellant, for example, at a concentration of about 3% to about 25% of the total composition.

According to one or more embodiments of the present invention, the foamed composition has specific gravity of about 0.02 gr/ml to about 0.35 gr/ml.

According to one or more embodiments of the present invention, iodine is selected from molecular iodine and complexed iodine. Complexed iodine may be selected from cadexomer-iodine, diiodhydrin, domiodol, hydriodic acid, iodinated glycerol, iodoform, iodide and povidone-iodine According to one or more embodiments of the present invention, the solvent is water or a water miscible organic solvent, such as a polyhydroxy compounds and poly-ethoxylated compounds. In one embodiment the composition has a water-to-water miscible organic solvent ratio of about 1:10 to about 10:1. Due to the skin irritability of lower alkyl alcohols, the water miscible compound is not a lower alkyl, e.g., $C_1$-$C_5$, alcohol.

In one or more embodiments, the polyhydroxy compound is selected from ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether and mixtures thereof.

In one or more embodiments, the poly-ethoxylated compound is selected from polyethylene glycol, tetrahydrofurfuryl alcohol and polyethyleneglycol. The solvent can be mixtures of water, polyhydroxy compounds and/or poly-ethyoxylated compounds.

According to one or more embodiments, a surface active agent may be an anionic surface active agent, a cationic surface active agent, a nonionic surface active agent, a zwitterionic surface active agent, an amphoteric surface active agent, an ampholytic surface active agent and mixtures thereof.

In one or more embodiments, the surface-active agent includes at least a non-ionic agent. In one or more embodiments, the surface active agent is a mixture of a non-ionic surface active agent and an anionic surface active agent provided at a weight ratio of about 4:1 to about 1:4 more preferably a weight ratio of about 2:1 to about 1:2. In one or more embodiments, the surface-active agent has a HLB value higher than about 8.

According to one or more embodiments, the foam adjuvant is selected from a fatty alcohol, a fatty acid mixtures thereof, and is provided at a concentration between about 0.4% and about 2.5% of the composition.

Another aspect the present invention provides a method of treating, alleviating or preventing a human or veterinary disorder by topically administering to a surface afflicted with the disorder an effective amount of the composition according to one or more embodiments of the present invention.

The method of the invention, according to one or more embodiments, provides for the prophylaxis, or treatment of or alleviation of the symptoms of a variety of infectious dermatological disorders, including for example heat burns, chemical burns, infections, wounds, cuts and ulcers and radioactive radiation damage, and burns and infections resulting from chemical and biological warfare agents.

BRIEF DESCRIPTION OF THE DRAWING

The invention is described with reference to the FIGURE, which is provided for the purpose of illustration only and is not intended to be limiting of the invention.

The FIGURE is an illustration of a foam dispenser used in one or more embodiments of the present invention.

DETAILED DESCRIPTION OF THE INVENTION

Composition

Figure 1:
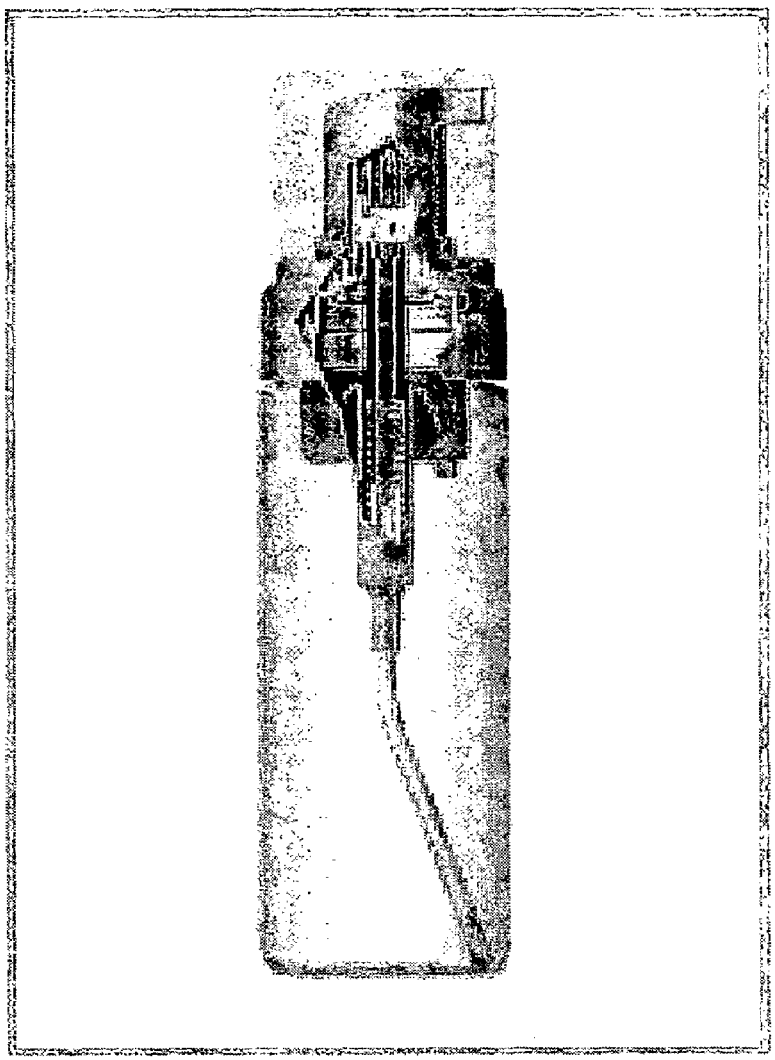

According to one aspect, the present invention provides a foamable composition of matter includes iodine, water, a foam adjuvant, a surface active agent and a gelling agent, in the following concentrations, reported as percent by weight:
- iodine: about 0.1% to about 5%;
- at least one solvent: about 80% to about 99.6%;
- at least one foam adjuvant: about 0.1% to about 5%;
- at least one surface active agent: about 0.1% to about 5%; and
- at least one gelling agent: about 0.1% to about 5%.

The % values presented herein are provided on a weight (w/w) basis of the total composition.

The composition according to one or more embodiments of the present invention is applied to the surface as a foam. That is, the foamed composition is applied to the substrate and is not generated by rubbing or lathering. The foamed composition, according to one or more embodiments of the present invention, is dispensed from a glass or plastic container that dispenses foam in the absence of a gas or liquid propellant.

Alternatively, the composition of the present invention further includes a liquefied or compressed gas propellant at a concentration of about 3% to about 25% of the total composition. Examples of suitable propellants include volatile hydrocarbons such as butane, propane, isobutane or mixtures thereof, and fluorocarbon gases.

The foamed composition, according to one or more embodiments of the present invention, is of exceptionally low specific gravity, for example, the foamed composition has a specific gravity in the range of about 0.02 gr/ml to about 0.35 gr/ml. Although of low specific gravity, the foam is highly stable and will remain without collapse for several minutes. Nonetheless, the foam collapses readily upon application of mild shear stress. Low specific gravity, high foam stability and ready collapsibility all contribute to a foamed composition that is easily applied and administered over large areas without rubbing or chaffing of the affected area.

Iodine

"Iodine" and "iodine species" include iodine in its native form or released from a compound. In its native form, iodine ($I_2$) is provided as bluish-black crystals, having density of about 5 g/cm$^3$. When used as is, the iodine concentration in the total composition ranges between 0.1% and 5% and more preferably, between 0.5% and 1.5%. In other embodiments of the present invention molecular iodine is released from an iodine-containing and/or producing compound. Non-limiting examples of such compounds include cadexomer-iodine, diiodhydrin, domiodol, hydriodic acid, iodinated glycerol, iodide, iodoform, and povidone-iodine. When provided as an iodine-containing and/or producing compound, the compound concentration in the total composition is calculated to achieve a final iodine concentration ranging between about 0.1% and 5% by weight and more preferably, between about 0.5% and about 1.5% by weight.

Solvent

According to one or more embodiments, the composition includes about 80% to about 99.6% solvent, and typically includes water. Iodine is not highly soluble in water and thus, formulation stability and effectiveness is limited. In a one or more embodiments of the present invention, the solvent includes water and a water miscible organic solvent, which by way of non-limiting examples, is a polyhydroxy compound and/or a poly-ethoxylated compound.

Suitable polyhydroxy solvents (polyols) include small organic molecules having two or more hydroxy groups on their carbon skeleton, such as ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether (Transcutol®) and mixtures thereof.

Poly-ethoxylated compounds can enhance the effectiveness of iodine significantly by dissolving the $I_2$. Examples of suitable poly-ethoxylated compounds include polyethylene glycol (e.g., PEG 400), tetrahydrofurfuryl alcohol polyethyleneglycol ether (glycofurol, tetraglycol (TG)). Among the above-mentioned water miscible solvents, suitable compounds include transcutol, polyethylene glycol and TG and mixtures thereof. The ratio between water and the water miscible solvents is in the range of about 1:10 to about 10:1. In one or more embodiments, the ratio is between about 1:4 and about 4:1. Due to the skin irritability of lower alkyl (C1-C5) alcohols, and the tendency of such alcohols to impair the natural skin barrier by dissolving and removing the oily components of the skin, lower alkyl alcohols are not included as a miscible organic solvent.

Foam Adjuvant

A foam adjuvant is included in the composition to improve the stability and reduce the specific gravity of the foamed composition. In one or more embodiments of the present invention, foam adjuvants include fatty alcohols, fatty acids, and mixtures thereof. The foam adjuvant can include at least one fatty alcohol and at least one fatty acid.

Suitable fatty alcohols include alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). The concentration of the fatty alcohol required to support the foam system is inversely related to the length of its carbon chains. Fatty alcohols that are derived from beeswax, including a mixture of alcohols, a majority of which has at least 20 carbon atoms in their carbon chain, are especially well suited as foam adjuvants according to the present invention. The concentration of the fatty alcohol required to support the foam system is inversely related to the length of its carbon chains.

Suitable fatty acids include acids having 16 or more carbons in its carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the concentration of fatty acids required to support the foam system is inversely proportionate to carbon chain length.

Optionally, the carbon atom chain of the fatty alcohol or the fatty acid may have at least one double bond. A further class of foam adjuvant agent includes a long chain fatty alcohol or fatty acid, wherein the carbon atom chain is branched. The carbon chain of the fatty acid or fatty alcohol can be substituted with a hydroxyl group, such as 12-hydroxy stearic acid.

The foam adjuvant of the present invention may include a mixture of fatty alcohols, fatty acids and hydroxy fatty acids and alcohols in any proportion. The total amount of foam adjuvants is about 0.1% to about 5% (w/w) of the carrier mass, and typically, the total amount is about 0.4% to about 2.5% (w/w) of the carrier mass.

In one or more embodiments of the present invention, a fatty alcohol possesses a therapeutic properties per se. Long chain saturated and mono unsaturated fatty alcohols, e.g., stearyl alcohol, erycyl alcohol, arachidyl alcohol and docosanol have been reported to possess antiviral, anti infective, anti-proliferative and anti-inflammatory properties (U.S. Pat. No. 4,874,794). Longer chain fatty alcohols, e.g., tetracosanol, hexacosanol, heptacosanol, octacosanol, triacontanol, etc. are also known for their metabolism modifying properties and tissue energizing properties. Long chain fatty acids have also been reported to possess anti-infective characteristics. Thus, the iodine foamable composition of the present invention, containing the foam adjuvant provides a synergistic therapeutic benefit in comparison with currently used vehicles, which are inert and non-active.

Surface-active Agent

According to one or more embodiments of the present invention, the surface-active agent includes any agent linking oil and water in the composition, e.g., the agent can be a surfactant. In one or more embodiments of the present invention, the composition includes about 0.1% to about 5% of the surface-active agent.

Suitable surface-active agents include anionic, cationic, nonionic, zwitterionic, amphoteric and ampholytic surfactants, as well as mixtures of these surfactants. Such surfactants are well known to those skilled in the pharmaceutical and cosmetic formulation art. Non-limiting examples of useful surfactants include sucrose esters, sorbitan esters, PEG esters or ethers of fatty chains, mono or diglycerides, isoceteth-20, sodium methyl cocoyl taurate, sodium methyl oleoyl taurate, sodium lauryl sulfate, triethanolamine lauryl sulfate and betaines (e.g., cocamidopropyl betaine and lauramidopropyl betaine), which are known to contribute to foam stability (foam boosters).

While any surface-active agent may be used in the present invention, a surface-active agent having an HLB (hydrophilic-lipophilic balance) higher than 8 is used in one or more embodiments of the present invention.

Non-ionic surfactants are particularly well suited as surface-active agents. A combination of a non-ionic surfactant and an anionic surfactant (such as sodium lauryl sulfate) may also be used. A ratio of non-ionic surfactant to anionic surfactant between around 4:1 and about 1:4, or between about 2:1 and about 1:2, provides a foam, which upon rubbing onto the skin collapses easily, to allow facile spreading and absorption. A surface-active agent mix is even further improved when a foam stabilizing surfactant, such as cocamidopropyl betaine, is added.

Gelling Agent

In one or more embodiments of the present invention, the composition includes about 0.1% to about 5% of a gelling agent. Suitable gelling agents include, in a non-limiting manner, naturally-occurring polymeric materials such as locust bean gum, guar gum, sodium alginate, sodium caseinate, egg albumin, gelatin agar, carrageenin gum, sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Also useful herein are gelling agents such as the acrylic acid/ethyl acrylate copolymers and the carboxyvinyl polymers sold, for example, by the B.F. Goodrich Company under the trademark of Carbopol® resins. These resins include a colloidal water-soluble polyalkenyl polyether cross linked polymer of acrylic acid cross linked with from 0.75% to 2% of a cross linking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid cross linked with about 1% of polyallyl ether of sucrose having an average of about 5.8 allyl groups for each sucrose molecule.

Methods of Evolving and Releasing the Foam

Any customary method of evolving foam is applicable according to the present invention. By way of example, in one optional configuration, the composition according to one or more embodiments of the present invention is preferably placed, together with a liquefied or compressed gas propellant in the amount of about 3% to about 25% of the total composition, in an aerosol container. Upon pressing the actuator, a breakable foam, suitable for topical administration is released. Due to the oxidizing nature of iodine, containers that are coated with highly durable lacquers of coatings are used.

In an alternative exemplary configuration, the composition according to one or more embodiments of the present invention is placed in a plastic or glass container, equipped with a foaming dispenser that works without gas propellants. Such dispensers are described, for example, in U.S. Pat. No. 6,536,629, in which the dispenser includes a container and a dispensing assembly coupled in liquid-tight manner. The dispensing assembly can have a liquid pump with a liquid inlet and a liquid outlet. An exemplary foam dispenser is shown in the FIGURE.

Foam Characteristics

The foam that is released from the aerosol container or from the propellant-free foaming dispenser is well aerated. It has specific gravity of about 0.02 gr/ml to about 0.35 gr/ml. When applied onto a surface, specifically a skin surface, and rubbed gently, it spreads easily over the area, without the need of extensive rubbing.

A foam composition of one or more embodiments of the present invention is advantageous over formulation options. A foamed composition may possess one or more of the following properties. The foam is lightweight and thus, economical. The foam is easily spreadable, allowing treatment of large areas such as the arms, back, legs and the breast. The flow properties provide a foam that spreads effectively into folds and wrinkles, providing uniform distribution of the active agent without the need of extensive rubbing and absorbs into the skin. The low specific gravity, e.g., fluffy, nature of the foam renders application of the foam on large skin areas very easy, irritation-free and painless.

Foam Applications

The compositions according to one or more embodiments of the present invention are useful in the various medicinal disciplines including human and veterinary medicine. More generally, the compositions according to the present invention can be used in situations where use of iodine is preferred including, but not limited to, medicine, industrial processes, diagnostics and environmental purposes.

Specifically, the compositions according to one or more embodiments of the present invention are useful as antiseptic compositions. The compositions may be further used to protect from, prevent, alleviate the symptoms of or cure a variety of infectious dermatological disorders, including: bacterial Infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma; fungal infections including dermatophyte infections, yeast infections; parasitic infections including scabies, pediculosis, creeping eruption and viral infections.

The treatment of heat burns, chemical burns (caused by chemicals such as acids, bases, caustic materials and warfare chemicals), wounds, cuts and ulcers using the composition according to one or more embodiments of the present invention is particularly advantageous. Upon application, the foam spreads easily, covering the surface of the affected area, and without causing pain.

The composition of the invention is also useful as a protectant in case of exposure to radiation and radioactive isotopes.

According to another aspect the present invention provides a method of treating, alleviating or preventing a human or veterinary disorder by topically administering to a surface afflicted with the disorder an effective amount of the composition including:
  about 0.1% to about 5% by weight iodine;
  about 80% to about 99.6% by weight of at least one solvent;
  about 0.1% to about 5% by weight of at least one foam adjuvant;
  about 0.1% to about 5% by weight of at least one surface active agent; and
  about 0.1% to about 5% by weight of at least one gelling agent.

The present invention provides for the prophylaxis, or treatment of or alleviating the symptoms of a variety of infectious dermatological disorders, including heat burns, chemical burns, infections, wounds, cuts and ulcers and radioactive radiation damage, and burns and infections resulting from chemical and biological warfare agents.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Foamable Iodine Composition

The table below lists the components of the foamable composition.

| Ingredient | % (w/w) | Function |
| --- | --- | --- |
| Iodine ($I_2$) | 1% | Active agent |
| Purified Water | 64.3% | Water |
| Glycofurol | 30% | Water miscible solvent |
| Stearyl alcohol | 1% | Foam adjuvant |

-continued

| Ingredient | % (w/w) | Function |
| --- | --- | --- |
| Sodium Lauryl Sulfate | 1% | Surface active agent |
| Sucrose Ester 70 | 1% | Surface active agent |
| Cocamidopropyl Betaine | 0.5% | Surface active agent |
| Methocel LV15 (Hydroxypropylmethyl cellulose) | 0.8% | Gelling agent |
| Xanthan Gum | 0.4% | Gelling agent |

Iodine was dissolved in a mixture of glycofurol and stearyl alcohol and the mixture was heated to ~60 C until homogeneity was obtained. Methocel was dispersed in one third portion of water, preheated to 80° C., and sucrose ester was added. The remaining two-third portion of water at room temperature was added under vigorous stirring; and xanthan gum and sodium lauryl sulfate and cocamidopropyl betaine were added mixing continuously for 15 minutes under vigorous stirring. The iodine mixture was added carefully to aqueous mixture and was stirred for an additional 5 minutes for complete homogeneity. The resultant product was cooled to room temperature and filled into bottles.

EXAMPLE 2

Pressurized Foam Comprising Iodine

The composition of Example 1 (50 ml) at ambient temperature was added to a 125 ml aerosol container, the container was sealed with an aerosol valve and a butane/propane propellant (about 16% of the composition mass) was compressed into the container. Upon pressing the aerosol valve, a rich foam having specific gravity of about 0.1 gr/ml was released.

EXAMPLE 3

Iodine Non-pressurized Foam

The composition of Example 1 (50 ml) at ambient temperature was added to a 125 ml container, equipped with a foaming dispenser that works without gas propellants (Airspray International Inc., 3768 Park Central Blvd. North, Pompano Beach, Fla. 33064, USA). Upon pressing the aerosol valve, rich foam having specific gravity of about 0.1 gr/ml to about 0.3 gr/ml was released.

What is claimed is:
1. A foamable composition comprising
  a. about 0.1% to about 5% by weight iodine;
  b. about 80% to about 99.6% by weight of at least one solvent;
  c. about 0.1% to about 5% by weight of at least one foam adjuvant comprising at least one fatty alcohol, at least one fatty acid, or a mixture thereof; and
  d. about 0.1% to about 5% by weight of at least one surface active agent; and
  e. a liquefied or compressed gas propellant, wherein the weight ratio of the propellant to the remainder of the composition is about 3:97 to about 25.75, said composition housed in a pressurized container comprising a valve configured to release said composition as breakable foam.
2. The composition claim 1, having specific gravity of about 0.02 gr/ml to about 0.35 gr/ml.
3. The composition of claim 1, wherein the iodine is selected from native iodine and complexed iodine.

4. The composition of claim 3, wherein the complexed iodine is selected from cadexomer-iodine, diiodhydrin, domiodol, hydriodic acid, iodinated glycerol, iodoform, and povidone-iodine.

5. The composition of claim 1, wherein the at least one solvent comprises water.

6. The composition of claim 5, further comprising a water miscible organic solvent.

7. The composition of claim 6, wherein the water miscible organic solvent is selected from the group consisting of a polyhydroxy solvent and a poly-ethoxylated compound.

8. The composition of claim 7, wherein the polyhydroxy solvent is selected from the group consisting of ethylene glycol, propylene glycol, glycerol, butanediols and isomers thereof, pentaerythritol, sorbitol, mannitol, dimethyl isosorbide, polyethylene glycol, polypropylene glycol, diethylene glycol monoethyl ether and mixtures thereof.

9. The composition of claim 7, wherein the poly-ethoxylated compound is selected from the group consisting of polyethylene glycol, tetrahydrofurfuryl alcohol and polyethyleneglycol.

10. The composition of claim 6, wherein the water to water miscible organic solvent ratio is in the range of about 1:10 to about 10:1.

11. The composition of claim 1, wherein the at least one surface active agent is selected from the group consisting of anionic surface active agents, cationic surface active agents, nonionic surface active agents, zwitterionic surface active agents, amphoteric surface active agents, ampholytic surface active agents and mixtures thereof.

12. The composition of claim 11, wherein the at least one surface-active agent is a mixture of a non-ionic surface-active agent and an ionic surface-active agent.

13. The composition of claim 12, wherein the non-ionic surface active agent to ionic surface active agent weight ratio is in the range of about 4:1 to about 1:4.

14. The composition of claim 12, wherein the non-ionic surface acting agent to ionic surface acting agent weight ratio is in the range of about 2:1 to about 1:2.

15. The composition of claim 11, wherein the at least one surface-active agent has a HLB value higher than about 8.

16. The composition of claim 1, wherein the at least one foam adjuvant is selected from a fatty alcohol, a fatty acid and a hydroxy fatty acid and mixtures thereof.

17. The composition of claim 1, wherein the at least one foam adjuvant comprises between about 0.4% and about 2.5% of the composition.

18. The composition of claim 1, wherein the at least one surface active agent is a nonionic surface active agent.

19. The composition of claim 12, wherein the ratio of non-ionic to ionic surface active agent is about 3:2.

20. The composition of claim 12, wherein the ionic surface active agent comprises a zwitterionic surface active agent and the ratio of zwitterionic to non-ionic surface active agent is about 1:2.

21. The composition of claim 12, wherein the ionic surface active agent comprises an anionic surface active agent and the amount of anionic surface active agent is about the same as or is less than the amount of non-ionic surface active agent.

22. The composition of claim 1, further comprising about 0.1% to about 5% by weight of at least one gelling agent.

23. The composition of claim 22, wherein the at least one gelling agent comprises naturally-occurring polymeric materials, chemically modified starches, semi-synthetic polymeric materials, synthetic polymeric materials, acrylic acid/ethyl acrylate copolymers and carboxyvinyl polymers.

24. The composition of claim 22, wherein the at least one gelling agent comprises locust bean gum, guar gum, sodium alginate, sodium caseinate, egg albumin, gelatin agar, carrageenin gum, sodium alginate, xanthan gum, quince seed extract, tragacanth gum, starch, a cellulose ether, hydroxypropyl guar gum, soluble starch, cationic cellulose, cationic guar, a carboxyvinyl polymer, polyvinylpyrrolidone, polyvinyl alcohol, a polyacrylic acid polymer, a polymethacrylic acid polymer, a polyvinyl acetate polymer a, a polyvinyl chloride polymer, a polyvinylidene chloride polymer, a polyalkenyl polyether cross-linked polymer of acrylic acid, or a mixture thereof.

25. The composition of claim 22, wherein the at least one gelling agent comprises hydroxypropylmethyl cellulose, hydroxyethyl cellulose, methyl cellulose, carboxymethyl cellulose, or a mixture thereof.

* * * * *

UNITED STATES PATENT AND TRADEMARK OFFICE
CERTIFICATE OF CORRECTION

| | |
|---|---|
| PATENT NO. | : 7,575,739 B2 |
| APPLICATION NO. | : 10/835359 |
| DATED | : August 18, 2009 |
| INVENTOR(S) | : Tamarkin et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1279 days.

Signed and Sealed this

Seventh Day of September, 2010

David J. Kappos
*Director of the United States Patent and Trademark Office*